United States Patent
Buehler

(10) Patent No.: US 10,492,535 B2
(45) Date of Patent: Dec. 3, 2019

(54) CONTAINERS FOR AEROSOL-GENERATING DEVICES

(71) Applicant: Philip Morris Products S.A., Neuchatel (CH)

(72) Inventor: Frederic Ulysse Buehler, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 110 days.

(21) Appl. No.: 15/544,544

(22) PCT Filed: Feb. 25, 2016

(86) PCT No.: PCT/EP2016/053940
§ 371 (c)(1),
(2) Date: Jul. 19, 2017

(87) PCT Pub. No.: WO2016/135224
PCT Pub. Date: Sep. 1, 2016

(65) Prior Publication Data
US 2018/0042303 A1 Feb. 15, 2018

(30) Foreign Application Priority Data
Feb. 26, 2015 (EP) ..................................... 15156713

(51) Int. Cl.
*A24F 47/00* (2006.01)
*A61M 15/06* (2006.01)
(Continued)

(52) U.S. Cl.
CPC ........... *A24F 47/008* (2013.01); *A61M 15/06* (2013.01); *B29D 23/14* (2013.01); *B29D 99/0053* (2013.01); *A61M 2205/02* (2013.01)

(58) Field of Classification Search
CPC ..................................................... A24F 47/008
See application file for complete search history.

(56) References Cited

U.S. PATENT DOCUMENTS

2010/0006113 A1  1/2010  Urtsev et al.
2011/0309157 A1  12/2011  Yang et al.
(Continued)

FOREIGN PATENT DOCUMENTS

CN  104135881 A  11/2014
EP  2 481 308 A1  8/2012
(Continued)

OTHER PUBLICATIONS

International Search Report and Written Opinion dated May 23, 2016 in PCT/EP2016/053940, filed Feb. 25, 2016.
(Continued)

*Primary Examiner* — James Harvey
(74) *Attorney, Agent, or Firm* — Oblon, McClelland, Maier & Neustadt, L.L.P.

(57) ABSTRACT

A container for an aerosol-generating device is provided, including a tubular compartment including a liquid compound source and being formed from a polymeric material; and at least one seal formed from the polymeric material and being configured to seal the tubular compartment, where a ratio of thermal conductivity per unit weight in a radial direction of the polymeric material to thermal conductivity per unit weight in a longitudinal direction of the polymeric material is greater than about 2, or where a ratio of thermal conductivity per unit weight in the longitudinal direction of the polymeric material to thermal conductivity per unit weight in the radial direction of the polymeric material is above about 2. An aerosol-generating system is also provided, including an aerosol-generating device configured to receive the container.

20 Claims, 6 Drawing Sheets

(51) Int. Cl.
  *B29D 23/14* (2006.01)
  *B29D 99/00* (2010.01)

(56) References Cited

U.S. PATENT DOCUMENTS

| | | | |
|---|---|---|---|
| 2012/0204889 A1 | 8/2012 | Xiu | |
| 2014/0123989 A1 | 5/2014 | Lamothe | |
| 2016/0309784 A1* | 10/2016 | Silvestrini | A61M 15/0066 |
| 2017/0095002 A1* | 4/2017 | Silvestrini | A24F 47/008 |
| 2017/0303581 A1* | 10/2017 | Schaller | A24F 47/008 |
| 2018/0010786 A1* | 1/2018 | Besso | A24F 47/008 |
| 2018/0014573 A1* | 1/2018 | Silvestrini | H05B 6/108 |
| 2018/0042303 A1* | 2/2018 | Buehler | A24F 47/008 |

FOREIGN PATENT DOCUMENTS

| | | |
|---|---|---|
| RU | 2 328 192 C1 | 7/2008 |
| WO | WO 2008/121610 A1 | 10/2008 |
| WO | WO 2013/178769 A1 | 12/2013 |
| WO | WO 2014/071329 A1 | 5/2014 |
| WO | WO 2014/140320 A1 | 9/2014 |

OTHER PUBLICATIONS

Extended European Search Report dated Sep. 30, 2015 in European Patent Application No. 15156713.8.
Kojiro Uetani, et al., "Elastomeric Thermal Interface Materials with High Through-Plane Thermal Conductivity from Carbon Fiber Fillers Vertically Aligned by Electrostatic Flocking", Advanced Materials, vol. 26 No. 33, Sep. 3, 2014, pp. 5857-5862.
"Polymers with High Thermal Conductivity", retrieved from the internet http://web.mit.edu/nanoengineering/research/polymers.shtml, Apr. 4, 2013, 2 Pages.
Taylor Soper, "PolyDrop turns Paint into Conductive Coatings, Wins $10K at UW Environmental Challenge", retrieved from the internet www.geekwire.com/2013/polydrop-turns-paint-conductive-coatings-wins-place-uw-enviornmental-challenge, Apr. 9, 2013, 6 Pages.
The Study for thermal-conductive graphene nanocomposites (9 Pages) http://www.cmfd.cnki.net/Journal/Issue.aspx?dbCode=CMFD&PYKM=BBBM&Year=2014&ssue=08&Volume=01&Page=89.
Chinese Office Action with English translation dated Aug. 6, 2019 in corresponding Chinese Patent Application No. 201680010449.3, (22 Pages).
Russian Notice of Allowance and Search Report with English translation dated Aug. 29, 2019 in corresponding Russian Patent Application No. 2017132850, (16 pages).

* cited by examiner

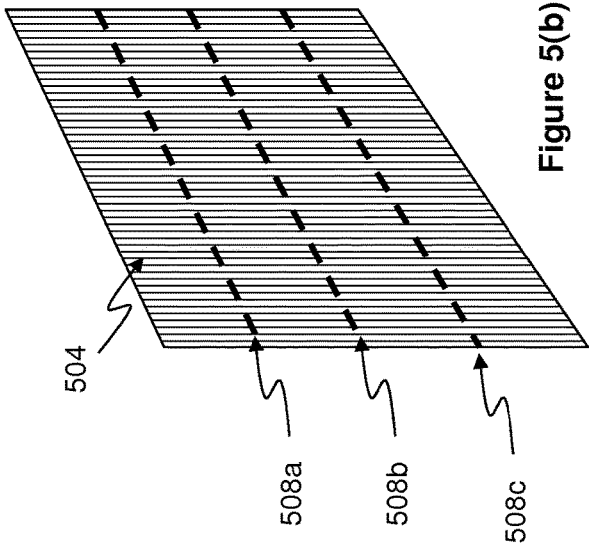
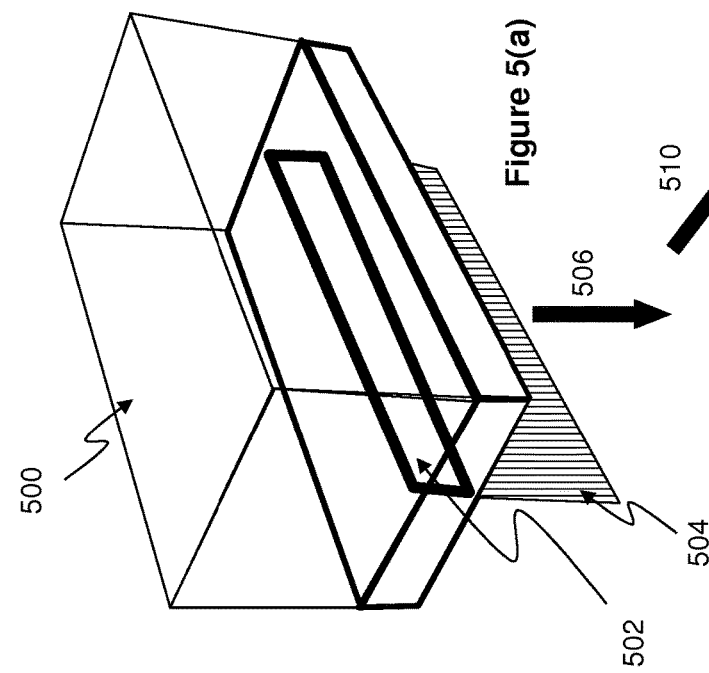
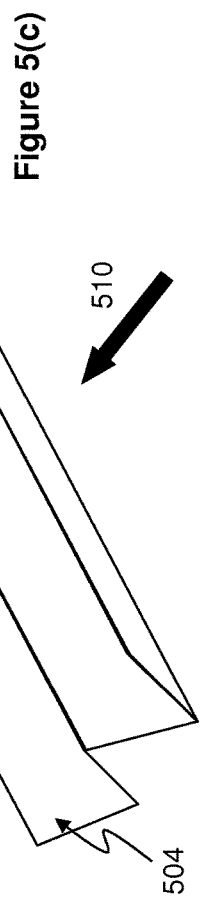

CONTAINERS FOR AEROSOL-GENERATING DEVICES

TECHNICAL FIELD

The present invention relates to a container for an aerosol-generating device, and to an aerosol-generating device configured to use the container to generate an aerosol. In particular, the invention relates to a container comprising reactants for forming aerosolised particles.

DESCRIPTION OF THE RELATED ART

Devices and methods for delivering nicotine or other medicament to a subject in which a delivery enhancing compound is reacted with nicotine or other medicament in the gas phase to form an aerosol of particles are known in the art. For instance, WO 2008/121610 A1 discloses a device in which a delivery enhancing compound and nicotine or other medicament are stored in separate reservoirs. The reactants, that is the delivery enhancing compound and the nicotine or other medicament, form liquid-vapour mixtures in the reservoirs. In use, the respective vapours are brought together to react with one another to form gaseous particles.

In order to improve storage of the liquid reactants, it has been proposed to use aluminium canisters within a disposable article for use in a device. The canisters are sealed using an aluminium foil, which is glued or welded to the ends of the canister. The use of aluminium canisters enables the volatile delivery enhancing compound and the nicotine or other medicament to be stored without substantial degradation by oxidation, hydrolysis or other unwanted reactions, which may alter the properties of the reactants. Furthermore, the use of aluminium provides suitable thermal conductivity to enable the stored compounds to be volatilised. However, forming an effective seal between the aluminium canister and the sealing foil is difficult. In addition, it has been found that the use of aluminium is not suitable for some delivery enhancing compounds, if significant shelf-life is required. Also, the manufacturing of canisters can be expensive.

It is therefore an object of the present invention to maintain at least some of the advantages associated with aluminium canisters while alleviating one or more of the above-mentioned drawbacks.

SUMMARY

According to a first aspect of the present invention, there is provided a container for an aerosol-generating device. The container comprises: a tubular compartment, comprising a liquid compound source, the tubular compartment being formed from a polymeric material; and, at least one seal, formed from a polymeric material, for sealing the tubular compartment. The ratio of [thermal conductivity per unit weight in the radial direction of the polymeric material] to the [thermal conductivity per unit weight in the longitudinal direction of the polymeric material] is greater than about 2.

BRIEF DESCRIPTION OF THE DRAWINGS

The invention will be further described, by way of example only, with reference to the accompanying drawings in which.

DETAILED DESCRIPTION

Figure 1:
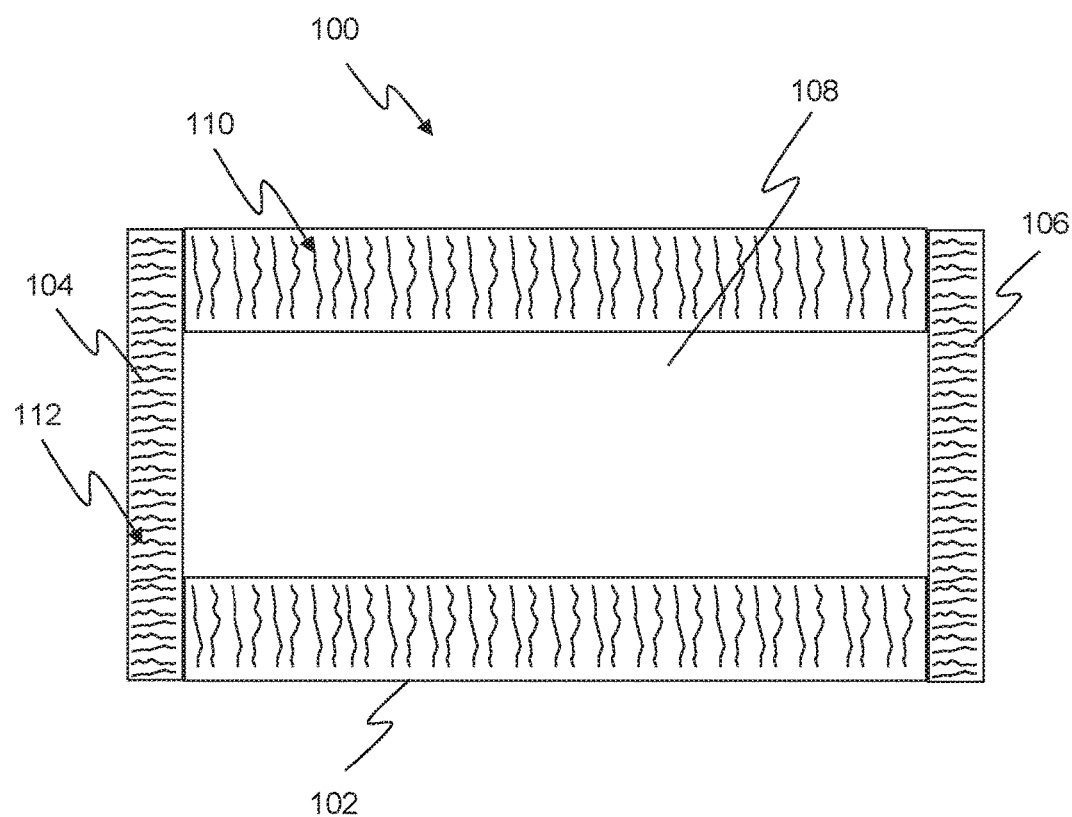
FIG. 1 shows a cross-sectional view of a container according to one embodiment of the present invention.

To provide a polymeric material having such a ratio of thermal conductivities the polymer chain backbones of the polymeric material forming the tubular compartment are preferably substantially aligned in the radial direction of the tubular compartment. By substantially aligned in the radial direction it is meant that the thermal conductivity of the polymeric material in the radial direction is substantially higher than the thermal conductivity of the same polymeric material in an amorphous state.

Forming the compartment from a polymeric material having the polymer chains substantially aligned in the radial direction may provide a container having improved thermal conductivity in the radial direction. That is to say, the transfer of heat from an external heater to liquid within the container can be improved as compared to a compartment formed from a polymeric material having randomly oriented polymer chains.

The use of a polymeric material may improve the shelf-life of the liquid compound because the polymeric material is preferably inert to the types of liquid compound which may be stored in the container.

In the first aspect of the invention, preferably the ratio of [thermal conductivity per unit weight in the radial direction of the polymeric material] to [thermal conductivity per unit weight in the longitudinal direction of the polymeric material] is preferably above about 10, preferably above about 50, more preferably above 100. The ratio of [thermal conductivity per unit weight in the radial direction of the polymeric material] to [thermal conductivity per unit weight in the longitudinal direction of the polymeric material] may be between about 20 and about 10,000.

Preferably, the thermal conductivity, in the radial direction, of the polymeric material is between about 70 W per meter Kelvin (W/(m·K)) and about 360 W per meter Kelvin (W/(m·K)) at 23° C. and a relative humidity of 50% as measured using the modified transient plane source (MTPS) method, more preferably, between 85 W per meter Kelvin (W/(m·K)) and about 150 W per meter Kelvin (W/(m·K)). Most preferably, the thermal conductivity, in the radial direction, of the polymeric material is between about 90 W per meter Kelvin (W/(m·K)) and about 115 W per meter Kelvin (W/(m·K)) at 23° C. and a relative humidity of 50% as measured using the modified transient plane source (MTPS) method.

Preferably, in the radial direction, the thermal conductivity per unit weight of the polymeric material is between about 40 W cm$^3$ per meter Kelvin gram (W cm$^3$/m·K·g) and about 250 W cm$^3$ per meter Kelvin gram (W cm$^3$/m·K·g), more preferably between about 75 W cm$^3$ per meter Kelvin gram (W cm$^3$/m·K·g) and about 200 W cm$^3$ per meter Kelvin gram (W cm$^3$/m·K·g). Most preferably, in the radial direction, the thermal conductivity per unit weight of the polymeric material is between about 100 W cm$^3$ per meter Kelvin gram (W cm$^3$/m·K·g) and about 150 W cm$^3$ per meter Kelvin gram (W cm$^3$/m·K·g).

In the first aspect of the present invention, the container preferably further comprises: a second tubular compartment, comprising a second liquid compound source. The second tubular compartment is preferably formed from a polymeric material. The container preferably comprise at least one second seal, formed from a polymeric material, for sealing the second tubular compartment. The container preferably comprise a hollow transfer section, longitudinally arranged between the tubular compartment and the second tubular compartment.

The second tubular compartment may be formed from a polymeric material having a ratio of [thermal conductivity per unit weight in the radial direction] to the [thermal conductivity direction per unit weight in the longitudinal] greater than about 2. The polymer chain backbones of the polymeric material are preferably substantially aligned in the radial direction of the second tubular compartment.

According to a second aspect of the present invention, there is provided a container for an aerosol-generating device. The container comprises: a tubular compartment, comprising a liquid compound source, the tubular compartment being formed from a polymeric material; a capillary wick extending into the sealed tubular compartment; and an electrical heater positioned adjacent the capillary wick. The ratio of [thermal conductivity per unit weight in the longitudinal direction of the polymeric material] to the [thermal conductivity per unit weight in the radial direction of the polymeric material] is above about 2.

The polymer chains of the polymeric material are preferably substantially aligned in the longitudinal direction of the tubular compartment. By substantially aligned in the longitudinal direction it is meant that the thermal conductivity of the polymeric material in the longitudinal direction is substantially higher than the thermal conductivity of the same polymeric material in an amorphous state.

Forming the compartment from a polymeric material having the polymer chains substantially aligned in the longitudinal direction a container may provide a container having improved thermal conductivity in the longitudinal direction. That is to say, the transfer of heat from one end of the container to the other end of the container can be improved as compared to a compartment formed from a polymeric material having randomly oriented polymer chains.

In the second aspect of the present invention, preferably the ratio [thermal conductivity per unit weight in the longitudinal direction of the polymeric material] to [thermal conductivity per unit weight in the radial direction of the polymeric material] is preferably above about 10, preferably above about 50, preferably above 100. The ratio [thermal conductivity per unit weight in the longitudinal direction of the polymeric material] to [thermal conductivity per unit weight in the radial direction of the polymeric material] may be between about 20 and about 10,000.

In the second aspect of the present invention, preferably the thermal conductivity, in the longitudinal direction, of the polymeric material is between about 70 W per meter Kelvin (W/(m·K)) and about 360 W per meter Kelvin (W/(m·K)) at 23° C. and a relative humidity of 50% as measured using the modified transient plane source (MTPS) method, more preferably, between 85 W per meter Kelvin (W/(m·K)) and about 150 W per meter Kelvin (W/(m·K)). Most preferably, the thermal conductivity, in the longitudinal direction, of the polymeric material is between about 90 W per meter Kelvin (W/(m·K)) and about 115 W per meter Kelvin (W/(m·K)) at 23° C. and a relative humidity of 50% as measured using the modified transient plane source (MTPS) method.

Preferably, in the longitudinal direction, the thermal conductivity per unit weight of the polymeric material is between about 40 W cm$^3$ per meter Kelvin gram (W cm$^3$/m·K·g) and about 250 W cm$^3$ per meter Kelvin gram (W cm$^3$/m·K·g), more preferably between about 75 W cm$^3$ per meter Kelvin gram (W cm$^3$/m·K·g) and about 200 W cm$^3$ per meter Kelvin gram (W cm$^3$/m·K·g). Most preferably, in the longitudinal direction, the thermal conductivity per unit weight of the polymeric material is between about 100 W cm$^3$ per meter Kelvin gram (W cm$^3$/m·K·g) and about 150 W cm$^3$ per meter Kelvin gram (W cm$^3$/m·K·g).

In the second aspect of the present invention, the container preferably further comprises: a second tubular compartment, comprising a second liquid compound source. The second tubular compartment is preferably formed from a polymeric material. The container preferably comprises at least one second seal, formed from a polymeric material, for sealing the second tubular compartment. The container preferably comprises a hollow transfer section, longitudinally arranged between the tubular compartment and the second tubular compartment.

In the second aspect of the present invention, the second tubular compartment may be formed from a polymeric material having a ratio of [thermal conductivity per unit weight in the longitudinal direction] to the [thermal conductivity per unit weight in the radial direction] greater than about 2.

The polymer chain backbones of the polymeric material are preferably substantially aligned in the longitudinal direction of the second tubular compartment.

As will be appreciated, any feature described with reference to the second aspect of the present invention is also, where appropriate, applicable to the first aspect of the present invention, and vice versa.

In conventional bulk polymers, the thermal conductivity is generally low, and of the order of 0.1 W/(m·K) to 0.3 W/(m·K). The thermal conductivity is generally so low because of the presence of defects within the bulk polymer material such as polymer chain ends, entanglement, randomly oriented polymer chains, voids and impurities. The defects act as phonon scattering sites for heat transfer, thus reducing the thermal conductivity. Such a material is therefore not appropriate for use in a container for aerosol-generating devices.

The present invention utilises a polymer material having a substantial proportion of the polymer chain backbones, i.e. the main chain of each polymer, aligned in one orientation. Such a material therefore has significantly less defects and thus the thermal conductivity may significantly be improved along the direction that the polymer chain backbones are aligned.

In addition, the use of a polymeric material, as compared to the use of known metallic materials, to form the container may advantageously reduce the weight of the container.

The material used to form the compartments may be a composite material comprising the polymeric material described herein and thermally conductive fibres. The thermally conductive fibres may be carbon fibres. The fibres are preferably aligned such that they are substantially perpendicular to the polymer chain backbones. Electrostatic flocking, or a similar process, may be used to align the fibres.

In the first or second aspect of the present invention, the compartment may be formed from a laminate material comprising the polymeric material and at least one layer of metallic material. Preferably, the polymeric material forms the internal surface of the compartment. The metallic layer may improve the barrier to oxygen, moisture and UV light. The metallic layer is preferably formed from aluminium.

The seal is preferably effected by heat-sealing a film of polymeric material to the container, or induction welding. Preferably the film is a thin-film, and is preferably frangible. The film may be a laminate comprising at least one layer of the polymeric material, and a layer of metal. The polymeric material is preferably provided on the internal surface of the film.

The polymeric material is preferably selected form the list consisting of ultra-high molecular weight polyethylene (UHMWPE), polyacetylene, polypyrolle, polyaniline, poly (p-phenylene vinylene), poly(3-alkylthiophenes), poly(thiophene), poly(3,4,-ethylenedioxythiophene), poly(p-phenylene sulphide), co-polymers thereof, and mixtures thereof.

Preferably, the polymeric material is ultra-high molecular weight polyethylene (UHMWPE). UHMWPE typically comprise long molecular chains with a molecular mass usually between 2 and 6 million Da, with each molecular chain comprising 100,000 to 250,000 monomers. The chain length may be between about 10 µm and about 40 µm.

To ensure the polymer chain backbones are substantially aligned in a single required direction, the material may be manufactured using a drawing process. Such a process may result in a material approximating a single crystal fibre, but in a bulk material. In one such process, the bulk material is manufactured from a gel at a first temperature, and then drawn under controlled tension at a second temperature. The first temperature may be 120 degrees C., and the second temperature may be 90 degrees C. The resulting polymer material may be in the form of a thin sheet, having the polymer chain backbones aligned along a parallel direction to the plane of the sheet. Therefore, without further processing of this thin sheet, forming the tubular compartment would result in a higher thermal conductivity per unit weight in the longitudinal direction than the radial direction.

Further processing of the thin sheet material by alternately folding the material with fold lines perpendicular to the aligned polymer chain backbone, and then pressing and heating the folded material to fuse the material together creates sheet material having the polymer chain backbones substantially aligned in a direction normal to the plane of the sheet material. Such material can then be used to form the tubular component having a higher thermal conductivity per unit weight in the radial direction than in the longitudinal direction.

UHMWPE is effectively odourless, tasteless and non-toxic, and has shown high resistance to most corrosive chemicals. Furthermore, UHMWPE has extremely low moisture absorption properties.

It has therefore been found that UHMWPE is particularly advantageous for use in storing the liquids as described below.

The bulk material may be formed into blocks, sheets, or can be moulded or extruded. If the bulk material is formed into blocks it can be further processed to form the compartment by machining, such as cutting, piercing or being formed in a lathe. If the bulk material is formed into sheets it can be formed into the compartment in conventional tube making processes, in particular methods for forming tubes from paper-based sheet material. For example, the tubes for the compartments may be formed by helically winding elongate sheet material onto a mandrel, the edges of the elongate sheet material abutting each other. Alternatively, the sheet material may be formed by winding consecutive layers of the sheet material onto the mandrel to build up the compartment.

The sheet material may be wound around a mandrel such that a seam is formed parallel to the longitudinal axis of the mandrel.

Processes enabling a tube to be formed of substantially infinite length may be preferred. The seal is preferably sealed to the compartment using one of: heat-sealing; and induction welding. Preferably, where the polymeric material is UHMWPE, the seal is sealed using heat-sealing.

The tubular compartment preferably comprises a liquid nicotine source. When present, the second tubular compartment preferably comprises a liquid delivery enhancing compound.

The use of a polymeric material to form the compartments may reduce or eliminate any degradation of the nicotine source, and more particularly may reduce or eliminate any degradation of the delivery enhancing compound, which may otherwise occur when the aluminium compartments of the prior art act as a catalyst. The use of polymeric material may also maintain a good barrier to oxygen, moisture and UV light, all of which may also cause the degradation of the compartment contents.

The compartments may be connected by an outer wrapper extending over the first compartment and the second compartment at least in a region extending either side of the abutting ends. The outer wrapper may extend substantially along the whole longitudinal length of the container.

As used herein, the term "longitudinal" is used to describe the direction between the downstream or proximal end and the opposed upstream or distal end of the container, aerosol-generating article or aerosol-generating device and the term "transverse" is used to describe the direction perpendicular to the longitudinal direction. The term "radial" is used to describe the direction extending away from the longitudinal axis of the container, aerosol-generating article or aerosol-generating device.

The container may further comprise a further portion, and a further transfer section arranged either between the first compartment and the further portion, or between the second compartment and the further portion. The further portion may be any appropriate function portion, including: a filter portion; a flavour portion; an aerosol-mixing chamber portion; and an aerosol-cooling portion.

The further portion may comprise a mouthpiece. The mouthpiece may be sealed at the downstream end of the container. The mouthpiece may comprise any suitable material or combination of materials. Examples of suitable materials include thermoplastics that are suitable for food or pharmaceutical applications, for example polypropylene, polyetheretherketone (PEEK) and polyethylene.

The container preferably comprises a first sealed compartment comprising a nicotine source, a second sealed compartment comprising a delivery enhancing compound, two transfer sections, and a filter section.

As will be appreciated, further compartments, or portions such as a mixing chamber or the like, can be provided.

As used herein, the terms 'upstream', 'downstream' and 'distal' and 'proximal' are used to describe the relative positions of components, or portions of components, of aerosol-generating articles, aerosol-generating devices and aerosol-generating systems according to the invention in relation to the direction of air drawn through the aerosol-generating articles, aerosol-generating devices and aerosol-generating systems during use thereof.

The upstream and downstream ends of the container are defined with respect to the airflow when a user draws on the proximal or mouth end of the container. Air is drawn into the aerosol-generating article at the distal or upstream end, passes downstream through the aerosol-generating articles and exits the aerosol-generating article at the proximal or downstream end.

The first compartment may comprise a tubular porous element. The nicotine source may be sorbed on the tubular porous element.

The second compartment may comprise a tubular porous element. Preferably, the delivery enhancing compound is sorbed on the tubular porous element.

As used herein, by "sorbed" it is meant that the delivery enhancing compound, or volatile liquid, is adsorbed on the surface of the tubular porous element, or absorbed in the tubular porous element, or both adsorbed on and absorbed in the tubular porous element.

The tubular porous element preferably has a longitudinal length of between about 5 mm and about 20 mm, more preferably of between about 8 mm and about 12 mm, and preferably the tubular porous element has a longitudinal length of about 10 mm.

The tubular porous element may be a hollow cylinder. The hollow cylinder is preferably a right circular hollow cylinder.

The second compartment preferably has a longitudinal length of between about 5 mm and about 50 mm, more preferably between about 20 mm and about 40 mm. The second compartment may have a longitudinal length of about 35 mm.

The volume of the first compartment and the second compartment may be the same or different. The volume of the first compartment may be greater than the volume of the second compartment.

The molar ratio of [nicotine comprised in the first compartment] to [delivery enhancing compound comprised in the second compartment] is preferably comprised between 5:1 to 1:5 and more preferably between 2:1 and 1:2.

The molar ratio of [nicotine comprised in the first compartment] to [organic acid comprised in the second compartment] is preferably comprised between 5:1 to 1:5 and more preferably between 2:1 and 1:2.

The molar ratio of [nicotine comprised in the first compartment] to [lactic acid comprised in the second compartment] is preferably comprised between 5:1 to 1:5 and more preferably between 2:1 and 1:2.

The first compartment comprises a nicotine source. As such, the nicotine source preferably comprises one or more of nicotine, nicotine base, a nicotine salt, or a nicotine derivative.

The nicotine source may comprise natural nicotine or synthetic nicotine. The nicotine source may comprise nicotine base, a nicotine salt, such as nicotine-HCl, nicotine-bitartrate, or nicotine-tartrate, or a combination thereof.

The nicotine source may further comprise an electrolyte forming compound. The electrolyte forming compound may be selected from the group consisting of alkali metal hydroxides, alkali metal oxides, alkaline earth metal oxides, sodium hydroxide (NaOH), calcium hydroxide (Ca(OH)$_2$), potassium hydroxide (KOH) and combinations thereof.

Alternatively or in addition, the nicotine source may further comprise other components including, but not limited to, natural flavours, artificial flavours and antioxidants.

Preferably, the first compartment comprises a liquid nicotine formulation. The liquid nicotine formulation may comprise pure nicotine, a solution of nicotine in an aqueous or non-aqueous solvent or a liquid tobacco extract. The liquid nicotine solution may comprise an aqueous solution of nicotine base, a nicotine salt, such as nicotine-HCl, nicotine-bitartrate, or nicotine-tartrate and an electrolyte forming compound.

The first compartment preferably comprises a volatile liquid nicotine source.

The second compartment preferably comprises a volatile delivery enhancing compound. As used herein, by "volatile" it is meant the delivery enhancing compound has a vapour pressure of at least about 20 Pa. Unless otherwise stated, all vapour pressures referred to herein are vapour pressures at 25° C. measured in accordance with ASTM E1194-07.

Preferably, the volatile delivery enhancing compound has a vapour pressure of at least about 50 Pa, more preferably at least about 75 Pa, most preferably at least 100 Pa at 25° C.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. Alternatively, the volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. Alternatively the volatile delivery enhancing compound may comprise a non-aqueous solution of one or more compounds.

The volatile delivery enhancing compound may comprise two or more different volatile compounds. For example, the volatile delivery enhancing compound may comprise a mixture of two or more different volatile liquid compounds.

Alternatively, the volatile delivery enhancing compound may comprise one or more non-volatile compounds and one or more volatile compounds. For example, the volatile delivery enhancing compound may comprise a solution of one or more non-volatile compounds in a volatile solvent or a mixture of one or more non-volatile liquid compounds and one or more volatile liquid compounds.

The delivery enhancing compound preferably comprises an acid. More preferably, the delivery enhancing compound comprises an acid having a vapour pressure of at least about 5 Pa at 20° C. Preferably, the acid has a greater vapour pressure than nicotine at 20° C.

The delivery enhancing compound may comprise an organic acid or an inorganic acid. Preferably, the delivery enhancing compound comprises an organic acid. More preferably, the delivery enhancing compound comprises a carboxylic acid. Most preferably, the carboxylic acid comprises a 2-oxo acid, or lactic acid. Preferably, the delivery enhancing compound comprises lactic acid. Other suitable acid includes aspartic acid, glutamic acid, salicylic acid, tartaric acid, gallic acid, levulinic acid, acetic acid, malic acid, citric acid, oxalic acid, sulphuric acid, palmitic acid, and alginic acid.

The 2-oxo acid comprises an acid may be selected from the group consisting of 3-methyl-2-oxovaleric acid, pyruvic acid, 2-oxovaleric acid, 4-methyl-2-oxovaleric acid, 3-methyl-2-oxobutanoic acid, 2-oxooctanoic acid and combinations thereof. The delivery enhancing compound may comprise pyruvic acid.

The tubular porous element is preferably a sorption element with an acid sorbed thereon.

The tubular porous element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

Where the second compartment comprises a tubular porous element, the tubular porous element may comprise one or more porous materials selected from the group consisting of porous plastic materials, porous polymer fibres and porous glass fibres. The one or more porous materials may or may not be capillary materials and are preferably inert with respect to the acid. The particular preferred porous material or materials will depend on the physical properties of the acid. The one or more porous materials may have any suitable porosity so as to be used with different acids having different physical properties.

Suitable porous fibrous materials include, but are not limited to: cellulose cotton fibres, cellulose acetate fibres and bonded polyolefin fibres, such as a mixture of polypropylene and polyethylene fibres.

The tubular porous element may have any suitable size and shape.

The size, shape and composition of the tubular porous element may be chosen to allow a desired amount of volatile delivery enhancing compound to be sorbed on the tubular porous element.

The tubular porous element advantageously acts as a reservoir for the delivery enhancing compound.

According to an aspect of the present invention, there is provided an aerosol-generating system. The system comprises a container as described above with reference to the first aspect of the present invention, and an aerosol-generating device configured to receive the container. The device comprises: a piercing member for piercing the or each container; and at least one tubular heater, for externally heating the or a compartment when the container is received in the device.

As used herein, the term "aerosol-generating device" refers to an aerosol-generating device that interacts with an aerosol-generating article, in this case a container as described herein, to generate an aerosol that is directly inhalable into a user's lungs thorough the user's mouth.

Where the container comprises two compartments, the compartments may be arranged in series. As used herein, by "series" it is meant that the first compartment and the second compartment are arranged within the container so that in use an air stream drawn through the container passes through one compartment and then passes through the other compartment. Preferably, air drawn through the container passes through the first compartment and then passes through the second compartment. Nicotine vapour is released from the nicotine source in the first compartment into the air stream drawn through the container and delivery enhancing compound vapour is released from the delivery enhancing compound in the second compartment. The delivery enhancing compound vapour reacts with the nicotine vapour in the gas phase to form an aerosol, which is delivered to a user.

Where the container comprises two compartments, the compartments may be arranged in parallel.

The aerosol-generating device preferably has at least one air inlet. As used herein, the term "air inlet" is used to describe one or more apertures through which air may be drawn into the aerosol-generating system.

As used herein, the term "air outlet" is used to describe one or more aperture through which air may be drawn out of the aerosol-generating system. Preferably, the air outlet is provided at the downstream end of the container.

Preferably, each of the first compartment and the second compartment comprises a frangible barrier at each end. The frangible barrier is configured such that the barrier can be pierced by the piercing member when the container is inserted into the aerosol-generating device by the user.

Preferably, the outer housing of the aerosol-generating device comprises a cavity configured to receive the container. Preferably, the cavity has a longitudinal length greater than the longitudinal length of the elongate piercing member. In this way, the piercing portion of the piercing member is not exposed, or accessible by the user.

Preferably, the cavity of the aerosol-generating device is substantially cylindrical. The cavity of the aerosol-generating device may have a transverse cross-section of any suitable shape. For example, the cavity may be of substantially circular, elliptical, triangular, square, rhomboidal, trapezoidal, pentagonal, hexagonal or octagonal transverse cross-section.

Preferably, the cavity of the aerosol-generating device has a transverse cross-section of substantially the same shape as the transverse cross-section of the container to be received in the cavity.

The device may further comprise a second tubular heater for externally heating the second compartment when the container is received in the device.

The aerosol-generating system may further comprise a power supply for providing power to the, when present, at least one heater, and control circuitry. The control circuitry is preferably configured to control the supply of power to the at least one heater such that the delivery enhancing compound and the nicotine source are sufficiently volatilised to enable the generation of an aerosol.

In use, the nicotine typically reacts with the acid in the gas phase, either in a transfer section or in the second compartment to form aerosolised nicotine salt particles.

It will be understood that the aerosol-generating system may also be regarded as an aerosol delivery system. That is to say, the aerosol-generating system provides means for the nicotine source, such as a nicotine formulation, and the delivery enhancing compound, such as a pyruvic acid or lactic acid, to mix and generate an aerosol but does not actively generate the aerosol.

Where the container comprises a filter section, the filter section may comprise a filtration material capable of removing at least a portion of any unreacted acid mixed with aerosolised nicotine salt particles drawn through the filter section. The filtration material may comprise a sorbent, such as activated carbon.

As will be appreciated, a number of factors influence the formation of the nicotine salt particles. In general, in order to control the nicotine delivery it is important to control the vaporisation of the nicotine formulation and the acid. It is also important to control the relative quantities of the nicotine and the acid. Preferably, the molar ratio of acid to nicotine in the aerosol forming chamber is about 1:1. The use of acid as a delivery enhancing compound has been found to approximately double the delivery rate of nicotine to a user for equivalent power supplied to the vaporiser.

The vaporisation of the acid is controlled by the concentration of the acid in the first compartment, and by the exchange surface area of acid in the second compartment. The vaporisation of the acid may be controlled by heating the second compartment of the container or by heating ambient air drawn through the device before it passes through the second compartment.

The container is preferably substantially cylindrical in shape. The container may have a transverse cross-section of any suitable shape. Preferably, the container is of substantially circular transverse cross-section or of substantially elliptical transverse cross-section. More preferably, the container is of substantially circular transverse cross-section.

Preferably, the container has a transverse cross-section substantially the same shape as the cavity of the aerosol-generating device.

The container may simulate the shape and dimensions of a tobacco smoking article, such as a cigarette, a cigar, a cigarillo or a pipe, or a cigarette pack. Preferably, the housing simulates the shape and dimensions of a cigarette.

The aerosol-generating device and container may be arranged to releasably lock together when engaged.

The outer housing of the device may be formed from any suitable material or combination of materials. Examples of suitable materials include, but are not limited to, metals, alloys, plastics or composite materials containing one or more of those materials. Preferably, the outer housing is light and non-brittle.

The aerosol-generating system and device are preferably portable. The aerosol-generating system may have a size and shape comparable to a conventional smoking article, such as a cigar or cigarette.

In a yet further aspect of the present invention, there is provided an aerosol-generating system. The system comprises a container as described above with reference to the second aspect of the present invention, and an aerosol-generating device configured to receive the container. The device comprises: a cavity for receiving the container; and a power supply for providing power to the at least one electrical heater.

The device preferably comprises electrical contacts, within the cavity, for coupling with corresponding electrical contacts preferably provided on the container.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

FIG. 1 shows a cross-sectional view of a container 100 for use in an aerosol-generating device. The container 100 comprises a hollow tubular compartment 102, a first seal 104 provided at a first end of the compartment and a second seal 106 provided at a second end of the compartment. The hollow interior 108 of the container comprises a liquid compound source, and in particular a volatile liquid nicotine source.

The hollow tubular compartment 102 is formed from ultra-high molecular weight polyethylene (UHMWPE). As represented, not to scale, in FIG. 1, the polymer chain backbones 110 of the UHMWPE are substantially aligned in the radial direction. The first seal 104 and the second seal 106 are also formed from UHMWPE. The polymer chain backbones 112 of the UHMWPE are substantially aligned in the longitudinal direction.

The alignment of the polymer chain backbones results the ratio of [thermal conductivity per unit weight in the radial direction of the polymeric material] to the [thermal conductivity per unit weight in the longitudinal direction of the polymeric material] being greater than about 2.

The UHMWPE material used to form the compartments reduces or eliminates any degradation of the liquid compound source, which may otherwise occur when the aluminium compartments of the prior art act as a catalyst. The use of UHMWPE also maintains a good barrier to oxygen, moisture and UV light, all of which may also cause the degradation of the compartment contents.

To ensure the polymer chain backbones are substantially aligned in a single required direction, the material is manufactured using a drawing process. Such a process may result in a material approximating a single crystal fibre, but in a bulk material. In one such process, the bulk material is manufactured from a gel at a first temperature, and then drawn under controlled tension at a second temperature. The first temperature may be 120 degrees C., and the second temperature may be 90 degrees C. The thermal conductivity of the UHMWPE can be controlled by controlling the draw ratio during manufacture. The thermal conductivity increases with draw ratio, and this is because the proportion of polymer chain backbones aligned in the direction of drawing increases with increasing draw ratio. Thus, the thermal conductivity of the bulk material approaches that of the ideal single crystal. One example of a manufacturing process for the polymer material is described in further detail below with reference to FIGS. 5(a) to 5(e).

The tubular elements of the compartment 102 may be formed by any suitable known method for forming tubes from sheet material, in particular methods for forming tubes from paper-based sheet material. Indeed, at least one advantage of the container is that it may be formed using known methods which are less complex and cheaper than the methods for forming the metal containers of the prior art.

In one example, the tubular elements are formed by helically winding elongate laminate material onto a mandrel, the long edges of the elongate sheet material abutting each other. In this way, a hollow tube may be formed of infinite length. Once the tube is formed it is cut to the required lengths for the compartments.

Figure 2:
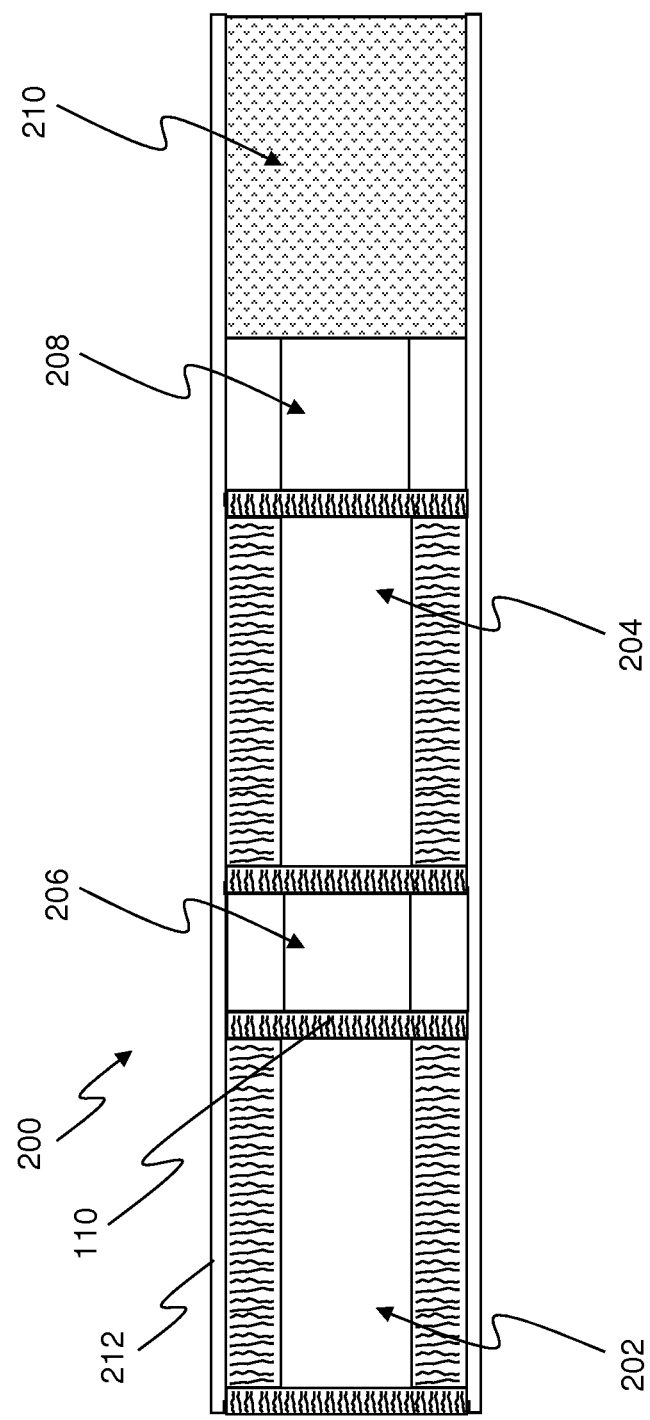
FIG. 2 show a schematic representation of an aerosol-generating article incorporating the container of FIG. 1.

FIG. 2 shows a schematic representation of an aerosol-generating article 200 incorporating two containers 202, 204 described with reference to FIG. 1. In addition, the aerosol-generating article 200 comprises a first transfer section 206, a second transfer section 208, and a filter section 210. The first container 202, second container 204, first transfer section 206, second transfer section 208 and the filter section 210 are combined together by an outer wrapper 212.

Each transfer section 206, 208 is formed from a hollow tube. The first transfer section 206 is provided in longitudinal abutting relationship between the first container 202 and the second container 204. The second transfer section 208 is provided in longitudinal abutting relationship between the second container 204 and the filter section 210.

Each seal of the first container and the second container is a frangible barrier. The frangible barriers are heat-sealed to the end faces of the respective compartments.

The filter section 210 may be any appropriate filter for use in a smoking article, such as a tow filter.

The first container 202 of the aerosol-generating article 200 comprises a nicotine source, and the second compartment 204 comprises a delivery enhancing compound, in particular a volatile liquid delivery enhancing compound comprising either pyruvic acid or lactic acid.

Figure 3:
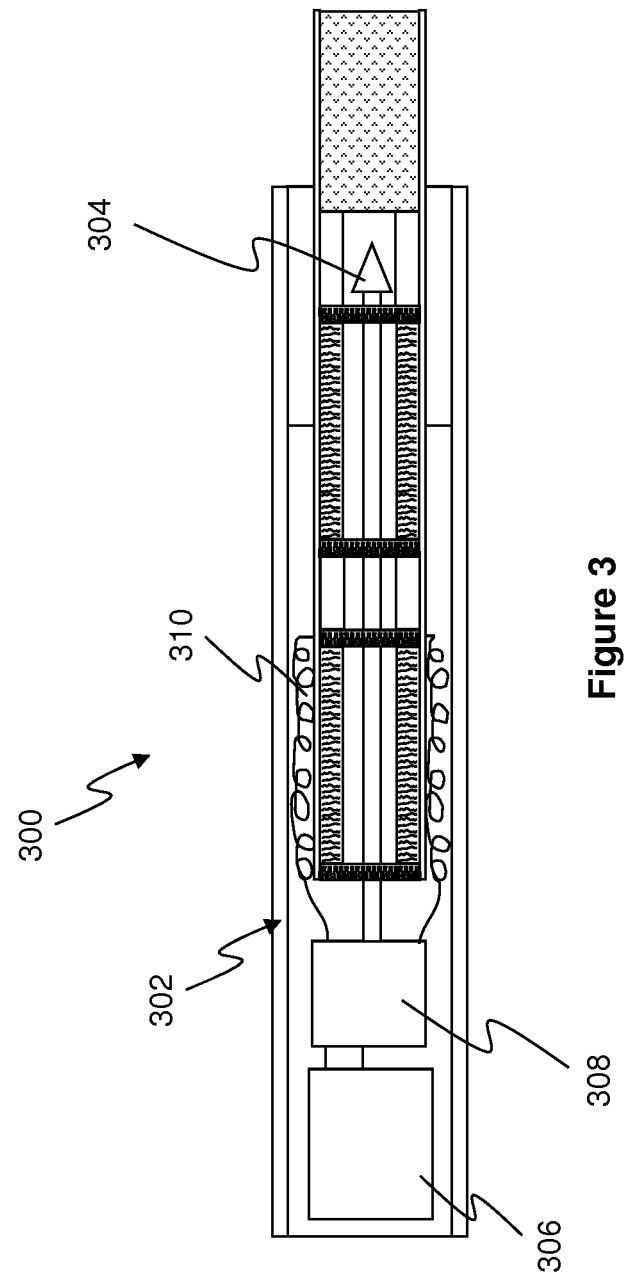
FIG. 3 shows a schematic representation of an aerosol-generating system according to one embodiment of the present invention.

FIG. 3 shows a cross-sectional view of an aerosol-generating system 300. The system 300 comprises an aerosol-generating device 302 and an aerosol-generating article 200 as described above. The aerosol-generating device 302 comprises an outer housing having an elongate cylindrical cavity configured to receive the aerosol-generating article 200. The longitudinal length of the cavity is less than the length of the container such that the proximal, or downstream, end of the aerosol-generating article protrudes from the cavity to form a mouthpiece.

The device 302 further comprises a piercing member 304. The piercing member is positioned centrally within the cavity of the aerosol-generating device and extends along the longitudinal axis of the cavity. At one end, the piercing member comprises a piercing portion in the form of a cone having a circular base. The piercing member further comprises a shaft portion. As can be seen, when the aerosol-generating article 200 is received within the aerosol-generating device, the piercing member is configured to pierce the frangible barriers of the first compartment and second compartment.

Air inlets (not shown) are provided at the upstream end of the aerosol-generating device 302. Air outlets (not shown) are provided at the proximal, downstream, filter end of the aerosol-generating article 200.

In use, the user applies a longitudinal force to the aerosol-generating article to insert it into the aerosol-generating device and pierce the frangible barriers with the piercing member 304. The piercing member 304 breaks the frangible barriers of the first compartment and second compartment and creates holes in the seals having a diameter approximately equal to the maximum diameter of the piercing portion. The maximum diameter of the piercing portion is the diameter of the base circle of the cone which forms the piercing portion.

As such, an airflow pathway is created extending from the air inlet (not shown) around the shaft of the piercing member 304, through the first compartment, through the transfer section, through the second compartment, through the second transfer section, exiting through the filter section.

In use, the volatile liquid nicotine vapour released from the volatile liquid nicotine source is entrained into the airflow as it passes through the first compartment. The air then continues through the transfer section, and then through the second compartment where the volatile delivery enhancing compound is entrained into the air flow as the user draws on the downstream end of the aerosol-generating article 200.

The delivery enhancing compound vapour reacts with the nicotine vapour in the gas phase to form an aerosol, which is delivered to the user through the proximal, downstream, end of the aerosol-generating article 200.

The aerosol-generating device 302 further comprises a power supply 306, control circuitry 308, and an electrical heater 310. The control circuitry 308 is configured to control the supply of power from the power supply 306 to the electrical heater 310. The electrical heater 310 is shown adjacent the first compartment, and is used to increase the temperature of the volatile liquid nicotine source to volatilise the nicotine at a rate such that the molar ratio of the nicotine vapour and the delivery enhancing compound vapour ensures a substantially complete reaction. In one example, the molar ration between the nicotine and the delivery enhancing compound where the delivery enhancing compound is lactic acid, 1:1.

Alternatively, or in addition, an electrical heater may be provided adjacent the second compartment. The control circuitry may be configured to heat the second compartment to a different temperature to the first compartment.

As described above in relation to FIG. 1, the polymer chain backbones 110 of the hollow tubular compartment 102 are substantially aligned in the radial direction. Manufacturing the tubular compartment from such a material significantly increases the thermal conductivity as compared to UHMWPE where the polymer chain backbones are substantially randomly oriented. The thermal conductivity is thus increased from about 0.4 W per meter Kelvin (W/(m·K)) to about 0.6 W per meter Kelvin (W/(m·K)) where the polymer chain backbones are substantially randomly oriented to about 100 W per meter Kelvin (W/(m·K)) to about 150 W per meter Kelvin (W/(m·K)). In comparison, the thermal conductivity of the prior art containers manufactured from aluminium is about 200 W per meter Kelvin (W/(m·K)). Therefore, it can be seen that the use of UHMWPE is feasible in terms of thermal conductivity, but provides the advantages of reducing or eliminating any degradation of the liquid compounds stored in the container, especially where the liquid is pyruvic acid or lactic acid.

Figure 4:
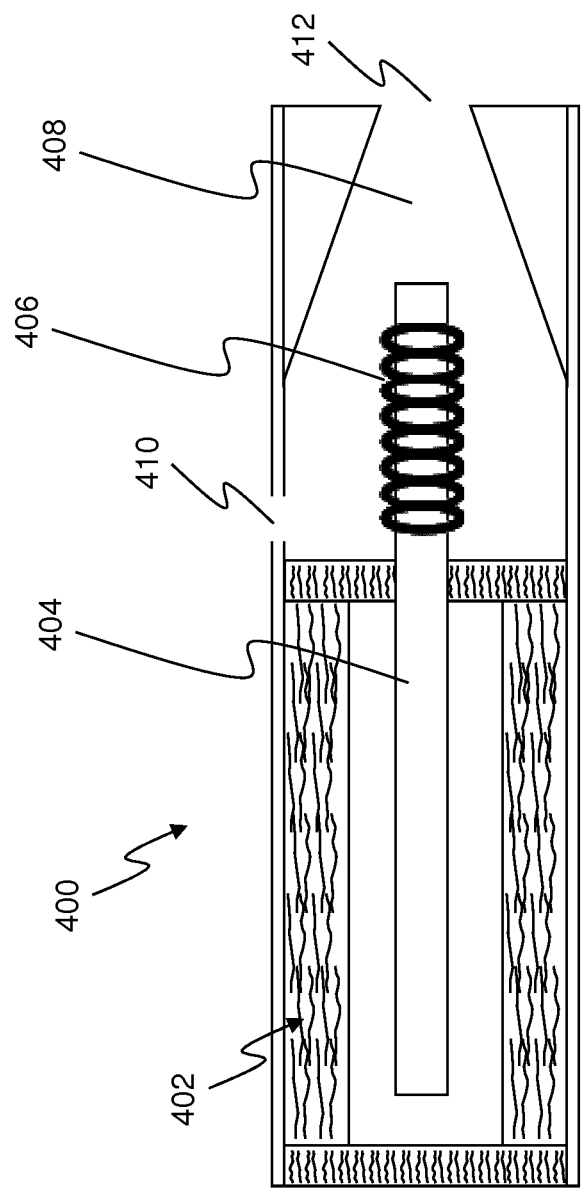
FIG. 4 shows a cross-sectional view of a container according to a further embodiment of the present invention.

An alternative aerosol-generating article 400, in the form of a replaceable cartridge for an aerosol-generating device, is shown in FIG. 4. The aerosol-generating article 400 comprises a container 402 comprising a liquid nicotine source, a capillary wick 404, an electrical heater 406, and an aerosol-forming chamber 408. The article 400 further comprises an air inlet 410 and an air outlet 412. The container 402 is similar to that described above with reference to FIG. 1, and is formed from UHMWPE. However, in this alternative, the polymer chain backbones are aligned in the longitudinal direction of the container. Again, the ends of the tubular compartment are sealed.

The aerosol-generating device configured to receive the article 400 comprises a power supply, control circuitry, and a cavity for receiving the article. In use, the user activates the device either using a power button, or by drawing on the downstream end of the article 400 to activate a puff sensor. The power supply then provides power to the electrical heater which aerosolises the liquid nicotine adjacent the heater on the capillary wick.

Providing a compartment formed from UHMWPE having the polymer chain backbones substantially aligned along the longitudinal direction enables the recuperation of dissipated heat from the electrical heater by conducting heat along the compartment more effectively, thus pre-heating the liquid within the compartment.

As described above, FIGS. 5(a) to 5(e) show one example of a manufacturing process for the polymer material having a thermal conductivity per unit weight in the radial direction greater than the thermal conductivity in the longitudinal direction.

FIG. 5(a) shows the extrusion process used to form a sheet of polymeric material having the polymer chain backbones substantially aligned in one direction. The tank 500 comprises a gel of polymeric material, which is extruded through the die 502 to form the sheet material 504. Tension 506 is then applied to the sheet material to further align the polymer chain backbones.

Figure 5D:
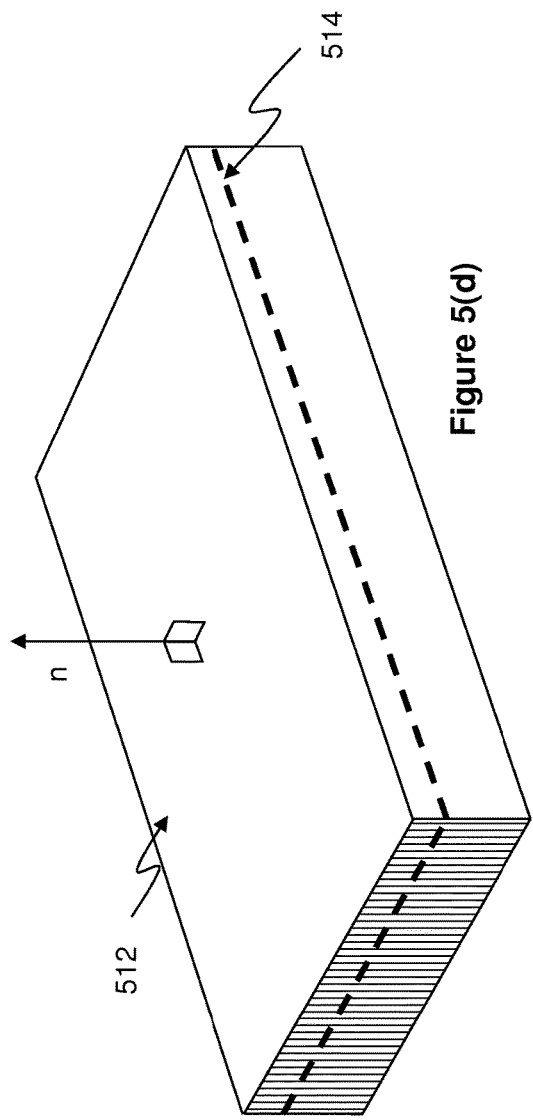
FIG. 5 show one example of a manufacturing process for forming a polymer material used to form the container of FIG. 1.
Figure 5E:
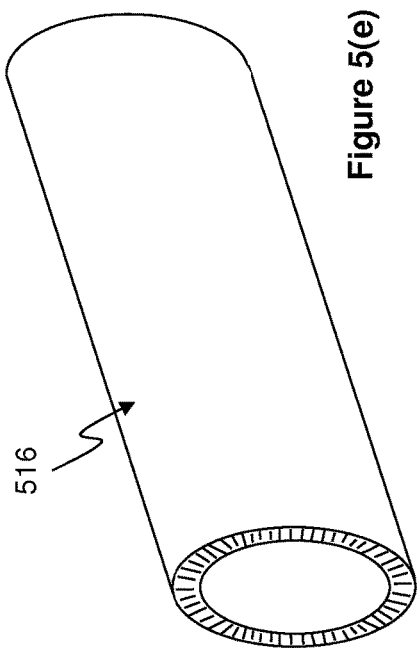

FIGS. 5(b) and 5(c) show the next stage of the manufacturing process where the sheet material 504 is alternately folded along fold lines 508a, 508b, and 508c. As can be seen, the fold lines are substantially perpendicular to the aligned polymer chain backbones. Thus the sheet material is folded using an accordion fold. Once the sheet material has been folded, pressure and heat 510 are applied to fuse the material into a block 512, as shown in FIG. 5(d).

The block 512 is then cut into thin sheets, for example along line 514. This process forms sheets of polymeric material having the polymer chain backbones aligned substantially perpendicular to the normal, n, of the plane of the sheet, as shown in FIG. 5(d).

The thin sheet material is then formed into a hollow tube 516 in any suitable manner as described above, and as shown in FIG. 5(e). The hollow tube thus has the polymer chain backbones aligned in the radial direction.

The invention claimed is:

1. A container for an aerosol-generating device, comprising:
    a tubular compartment, comprising a liquid compound source and being formed from a polymeric material; and
    at least one seal, formed from the polymeric material, and being configured to seal the tubular compartment,
    wherein a ratio of thermal conductivity per unit weight in a radial direction of the polymeric material to thermal conductivity per unit weight in a longitudinal direction of the polymeric material is greater than 2.

2. The container according to claim 1, wherein thermal conductivity of the polymeric material in the radial direction is between about 90 W/(m·K) and about 115 W/(m·K).

3. A container for an aerosol-generating device, comprising:
    a sealed tubular compartment, comprising a liquid compound source and being formed from a polymeric material;
    a capillary wick extending into the sealed tubular compartment; and
    at least one electrical heater disposed adjacent to the capillary wick,
    wherein a ratio of thermal conductivity per unit weight in a longitudinal direction of the polymeric material to thermal conductivity per unit weight in a radial direction of the polymeric material is above 2.

4. The container according to claim 3, wherein thermal conductivity of the polymeric material in the longitudinal direction is between about 90 W/(m·K) and about 115 W/(m·K).

5. The container according to claim 2, wherein the tubular compartment is formed from a laminate material comprising the polymeric material and at least one layer of metallic material.

6. The container according to claim 5, wherein the polymeric material forms an internal surface of the tubular compartment.

7. The container according to claim 2, wherein the polymeric material is ultra-high molecular weight polyethylene.

8. The container according to claim 2, wherein the at least one seal is sealed to the tubular compartment by heat-sealing or induction welding.

9. The container according to claim 2, wherein the liquid compound source comprises a nicotine source.

10. The container according to claim 2, further comprising:
    a second tubular compartment, comprising a second liquid compound source and being formed from the polymeric material;
    at least one second seal, formed from the polymeric material, and being configured to seal the second tubular compartment; and
    a hollow transfer section, longitudinally disposed between the tubular compartment and the second tubular compartment.

11. The container according to claim 10, wherein the second tubular compartment is formed from the polymeric material having the ratio of thermal conductivity per unit weight in the radial direction to thermal conductivity direction per unit weight in the longitudinal direction that is greater than about 2.

12. The container according to claim 10, wherein second tubular compartment is formed from the polymeric material having the ratio of thermal conductivity per unit weight in the longitudinal direction to thermal conductivity per unit weight in the radial direction that is greater than about 2.

13. The container according to claim 10, wherein the second liquid compound source comprises a delivery enhancing compound of pyruvic acid or lactic acid.

14. The container according to claim 3, wherein the tubular compartment is formed from a laminate material comprising the polymeric material and at least one layer of metallic material.

15. The container according to claim 14, wherein the polymeric material forms an internal surface of the tubular compartment.

16. The container according to claim 3, wherein the polymeric material is ultra-high molecular weight polyethylene.

17. The container according to claim 3, wherein the at least one seal is sealed to the tubular compartment by heat-sealing or induction welding.

18. The container according to claim 3, wherein the liquid compound source comprises a nicotine source.

19. The container according to claim 3, further comprising:
    a second tubular compartment, comprising a second liquid compound source and being formed from the polymeric material;
    at least one second seal, formed from the polymeric material, and being configured to seal the second tubular compartment; and
    a hollow transfer section, longitudinally disposed between the tubular compartment and the second tubular compartment.

20. An aerosol-generating system, comprising:
a container comprising:
- a tubular compartment, comprising a liquid compound source and being formed from a polymeric material, and
- at least one seal, formed from the polymeric material, and being configured to seal the tubular compartment,
- wherein a ratio of thermal conductivity per unit weight in a radial direction of the polymeric material to thermal conductivity per unit weight in a longitudinal direction of the polymeric material is greater than 2; and an aerosol-generating device configured to receive the container, comprising:
- a piercing member configured to pierce the container, and
- at least one tubular heater configured to externally heat the container or the tubular compartment when the container is received in the aerosol-generating device.

* * * * *